United States Patent
Schladenhauffen et al.

(10) Patent No.: US 7,763,746 B2
(45) Date of Patent: *Jul. 27, 2010

(54) PROCESS FOR CHEMICAL REACTIONS INVOLVING CYANOHYDRINS

(75) Inventors: Paul Benjamin Schladenhauffen, Houston, TX (US); Michael Stanley DeCourcy, Houston, TX (US); I-Hwa Midey Chang-Mateu, Ambler, PA (US); Robert Wilczynski, Yardley, PA (US); Donald Zolotorofe, Ivyland, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/284,028

(22) Filed: Sep. 18, 2008

(65) Prior Publication Data

US 2009/0082587 A1    Mar. 26, 2009

Related U.S. Application Data

(62) Division of application No. 11/268,372, filed on Nov. 7, 2005.

(60) Provisional application No. 60/630,872, filed on Nov. 24, 2004.

(51) Int. Cl.
    *C07C 255/00*    (2006.01)
(52) U.S. Cl. .................................... 558/451
(58) Field of Classification Search ............ 558/451
    See application file for complete search history.

(56) References Cited

U.S. PATENT DOCUMENTS

| 5,763,687 A | 6/1998 | Morisaki et al. |
| 6,743,938 B1 | 6/2004 | Croizy et al. |
| 2003/0208093 A1 | 11/2003 | Carlson, Jr. et al. |

FOREIGN PATENT DOCUMENTS

| DE | 765734 | 12/1952 |
| EP | 0226724 | 7/1987 |
| GB | 943536 | 12/1963 |

OTHER PUBLICATIONS

Schladenhauffen et al., Co-pending U.S. Appl. No. 11/268,372.*
R. Wilczynski, et al: "Kirk-Othmer Encyclopedia of Chemical Technology" 2003, John Wiley & Sons, Inc., XP002372018, vol. 16, Methacrylic acid and derivatives, p. 243-250.
*Encyclopedia of Chemical Technology*, by Kirk-Othmer, 4th Edition, vol. 16, John Wiley & Sons, 1995, pp. 16-18 and Figure 4.

* cited by examiner

*Primary Examiner*—James O. Wilson
*Assistant Examiner*—Paul V. Ward
(74) *Attorney, Agent, or Firm*—Marcella M. Bodner

(57) ABSTRACT

The present invention provides a method for minimizing the decomposition of cyanohydrins in exothermic chemical reactions involving cyanohydrins. The method comprises providing a reaction medium and reactants to a tubular reactor having internal mixing means, mixing the reaction medium and reactants to form a homogenous reaction mixture, removing heat from the reaction process and reacting the reactants to produce a mixed product having a bulk temperature. The method may further comprise cooling the reaction medium to a temperature from 1-10° C. cooler than the bulk temperature of the mixed product prior to providing the reaction medium to the tubular reactor.

12 Claims, 2 Drawing Sheets

PROCESS FOR CHEMICAL REACTIONS INVOLVING CYANOHYDRINS

Figure 1:
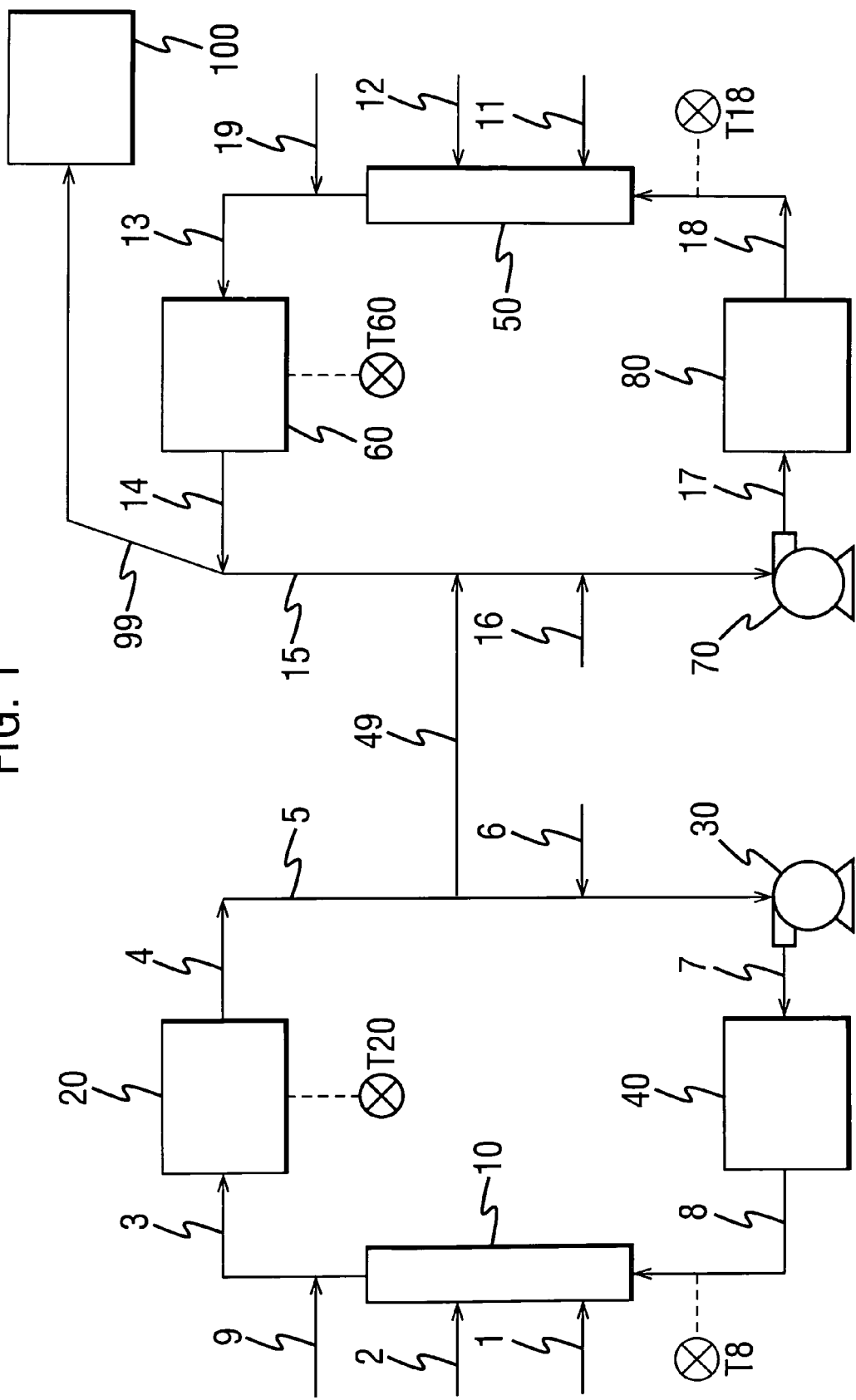

This non-provisional application is a divisional of non-provisional U.S. patent application Ser. No. 11/268,372, filed Nov. 7, 2005, now allowed, benefit of which is claimed under 35 U.S.C. §120 and which in turn claims benefit under 35 U.S.C. §119(e) of U.S. provisional Application No. 60/630,872, filed Nov. 24, 2004, priority benefit of which is also claimed for the present application.

The present invention relates to minimizing the thermal decomposition of cyanohydrins in chemical reactions involving cyanohydrins, such as hydrolysis reactions of acetone cyanohydrin, whereby overall product yields are increased.

There are many chemical processes which involve cyanohydrins, either as reactants or products. For example, well-known commercial processes for the production of methacrylic acid ("MAA") and esters thereof, such as methyl methacrylate ("MMA") and butyl methacrylate ("BMA"), from acetone cyanohydrin typically involve a series of reactions, including the initial hydrolysis reaction of acetone cyanohydrin with sulfuric acid. The process for production of MAA and esters of MAA also includes cracking of the hydrolysis products and further reaction, such as an acidification reaction to form MAA, or an esterification reaction to form esters of MAA. In addition, acetone cyanohydrin itself is the product of the reaction of acetone with hydrogen cyanide. The commercial market for MAA and esters thereof is extremely cost-sensitive and, therefore, any improvement in product yield, however slight, can result in significant cost-savings.

It is known that cyanohydrins are susceptible to decomposition in the presence of strong acids (e.g., sulfuric or phosphoric acid) or strong bases (e.g., caustic or diethylamine) to form hydrogen cyanide and other decomposition products (depending upon the nature of the cyanohydrin) at elevated temperatures, such as, for example, greater than about 70° C. Decomposition of cyanohydrin in reactions where the cyanohydrins are themselves the desired products results directly in decreased product yields. Decomposition of cyanohydrin in reactions where the cyanohydrins are intermediates or reactants in further reactions, such as in the production of MAA and its esters, indirectly results in decreased product yields, since a portion of the cyanohydrin is destroyed rather than being consumed by further reactions to produce the intended, desired reaction products. Thus, minimization of decomposition of cyanohydrin is an ongoing goal of chemical manufacturers whose reactions involve cyanohydrins.

It is also known that while higher temperatures generally increase the reaction rate of chemical reactions involving cyanohydrins, such reactions are also typically exothermic. Thus, in view of the potential for decomposition of cyanohydrins at high temperatures, strict control of the reaction temperature in processes involving cyanohydrins is important to maintain reaction rates while minimizing decomposition of the cyanohydrins.

One method known in the art for strictly controlling the reaction temperature of reactions involving cyanohydrins, including the hydrolysis reaction of acetone cyanohydrin with sulfuric acid, is to contain the reaction zone (where the reaction occurs) in one or more continuous stirred tank reactor ("CSTR"). CSTRs are typically well-agitated kettles or tanks and, for various reasons, a reaction process may include two or more CSTRs connected in series. CSTRs are often selected to contain reaction zones of particular chemical reactions requiring homogeneity because they are well-known and understood in the art to provide a homogenous reaction environment, i.e., where the reaction mixture composition and the reaction temperature are homogenous throughout the reaction zone. This means that the composition and temperature at which the reaction takes place within a CSTR is understood and assumed in the art to be the same as the composition and temperature at all locations within the CSTR, as well as the CSTR exit stream. Such uniformity of temperature and composition is helpful for optimizing the yield of chemical reactions, including those involving cyanohydrins, such as hydrolysis reactions of acetone cyanohydrin, in accordance with prior art methods.

For example, the Encyclopedia of Chemical Technology, by Kirk-Othmer, $4^{th}$ Edition, Vol. 16, John Wiley & Sons, 1995, pp. 16-18 and FIG. 4, teaches the preparation of MAA and its esters using the well-known process which begins with hydrolyzing acetone cyanohydrin with sulfuric acid in a CSTR. Similarly, U.S. Patent Publication No. 2003/0208093 (US '093) teaches a process for production of MAA and its esters wherein a series of two to three CSTR's are used for the hydrolysis reaction of acetone cyanohydrin with sulfuric acid. US '093 teaches that the hydrolysis reaction temperature is typically 70° C. to 135° C. (which means that the temperature of the bulk reaction mixture in the CSTR is 70° C. to 135° C.). According to the teachings of both documents, the hydrolysis reaction produces a hydrolysis mixture comprising α-sulfatoisobutyramide ("SIBAM"), α-hydroxyisobutyramide ("HIBAM"), and a lesser amount of methacrylamide ("MAM"). The hydrolysis mixture is subjected to a cracking reaction in which the SIBAM and HIBAM are converted to more MAM. The resulting MAM product may then be further reacted with water to produce MAA and with alkanols (e.g., methanol, butanol) to produce esters of MAA (e.g., MMA, BMA).

However, surprisingly and contrary to the general knowledge in the art, it has been discovered that where CSTRs are used in reactions involving cyanohydrins, such as the hydrolysis reaction of acetone cyanohydrin with sulfuric acid, persistent regions of high temperature occur in and around the location where the reactant feed is introduced into the CSTR (hereinafter, referred to as the "point of addition"). These localized regions of high temperature (herein referred to as "hot spots") may be up to 10° C., or even up to 20° C., higher than the otherwise uniform temperature of the bulk reaction mixture within the CSTR. These hot spots promote thermal decomposition of the cyanohydrin, thereby leading to a significant source of decreased product yields.

Thus, for example, in a process for the production of MAA and its esters, which involves the hydrolysis reaction of acetone cyanohydrin with sulfuric acid in a CSTR, where the reaction temperature is maintained within the presumably safe range of 80° C. to 90° C., the hot spot at the point of addition of the acetone cyanohydrin is greater than 90° C., which promotes the decomposition of the acetone cyanohydrin over the production of the preferred hydrolysis products (i.e., SIBAM, HIBAM and MAM) that are required for the further downstream reactions and ultimate production of MAA and its esters. Such irrecoverable yield losses can be as high as 3% and are, therefore, quite significant to the overall MAA and MAA ester production processes.

Out of all of the process variables in the hydrolysis reaction discussed above, studies have revealed that reaction temperature is the most significant with respect to acetone cyanohydrin decomposition. On average, laboratory experimentation by the applicants has revealed that acetone cyanohydrin decomposition decreases hydrolysis yield by about 1% for each 10° C. increase in hydrolysis reaction temperature. For example, in hydrolysis reactions of acetone cyanohydrin with sulfuric acid, conducted in a laboratory-scale CSTR, it was determined that an increase in the hydrolysis temperature of 10° C., from 85° C. to 95° C., resulted in an incremental 1% product yield loss.

Additionally, rapid and thorough mixing of the reactants with the reaction medium in the reaction zone is important for various reasons, including facilitating temperature control in reactions involving cyanohydrins. U.S. Pat. No. 5,763,687 discloses that thorough mixing in a chemical reaction for producing aromatic mononitro compounds can be achieved by the use of a tubular reactor having a particular internal configuration. More particularly, a plurality of twisted tabular members are arranged and positioned within the tubular reactor such that when reactants are fed to the reactor they are efficiently mixed as they pass through the reactor.

In view of the foregoing difficulties and shortcomings of conducting reactions involving cyanohydrins using CSTRs, which results in the newly discovered formation of a detrimental hot spot at the point of addition to the CSTR, there is a need for a method of conducting such reactions which minimizes the potential for decomposition of the cyanohydrins. The method of the present invention achieves this goal by using a reactor apparatus that ensures rapid and thorough mixing of the reactants with the reaction medium in the reaction zone and by manipulating the reaction temperature.

In a general embodiment of the present invention, a method for minimizing decomposition of cyanohydrins in an exothermic reaction process involving cyanohydrins is provided. The method comprises the steps of: (a) providing a reaction medium to a tubular reactor containing at least one reaction zone therein and having internal mixing means positioned in the at least one reaction zone; (b) providing one or more reactants to the tubular reactor; and (c) mixing the reaction medium with the one or more reactants in the at least one reaction zone, thereby forming a bulk reaction mixture having a substantially homogenous composition and a substantially homogenous reaction temperature. The exothermic reaction produces a quantity of heat and, therefore, the method of the present invention further comprises (d) removing a quantity of heat from the exothermic reaction process, the quantity of heat being equivalent to the quantity of heat produced by the exothermic reaction process; and (e) reacting the one or more reactants in the at least one reaction zone to produce a mixed product having a bulk temperature.

The tubular reactor may, in fact comprise two or more tubular reactors arranged in parallel or in series with one another. The internal mixing means of the tubular reactor may be at least one device selected from the group consisting of: static mixers, orifice plates, venturis, jet mixers, eductors, perforated plates, spargers, agitators, rotary mixers, high-velocity circulation loops, and spray nozzles. Furthermore, the reaction medium and the one or more reactants may be provided to the tubular reactor at a ratio of reaction medium:reactants of between 2:1 and 200:1.

In a particular embodiment of the present invention, the step of removing a quantity of heat may be performed by cooling the reaction medium to a temperature between 1° C. and 10° C. less than the bulk temperature prior to providing the reaction medium to the tubular reactor.

In another particular embodiment of the present invention, a first one of the one or more reactants may be provided to the tubular reactor in at least one of a plurality of points of addition by a plurality of injector devices positioned circumferentially about the tubular reactor apparatus. The step of mixing the reaction medium with the one or more reactants to form a homogeneous bulk reaction mixture may be accomplished, at least in part, by selecting and using one or more of the plurality of injector devices to provide the at least a first one of the one or more reactants to the tubular reactor.

In still another embodiment of the present invention, the exothermic reaction process involving cyanohydrins is a hydrolysis reaction, wherein a first reactant comprises acetone cyanohydrin, and a second reactant comprises an acid selected from the group consisting of: sulfuric acid, oluem and mixtures thereof. In this embodiment, the molar ratio of acid:acetone cyanohydrin present in the bulk reaction mixture may be in the range of from 1.3:1 to 1.9:1. Additionally, in this embodiment, the mixed product of the hydrolysis reaction may comprise one or more products selected from the group consisting of: $\alpha$-sulfatoisobutyramide, $\alpha$-hydroxyisobutyramide, and methacrylamide; and the method may further comprise: (f) thermally converting the mixed product from the hydrolysis reaction in a cracker reactor to produce a cracker reactor mixture comprising methacrylamide and methacrylic acid; and (g) reacting the cracker reactor mixture in at least one reactor with a material selected from alkanol and water to produce a monomer selected from methacrylic acid and esters thereof.

Figure 2:
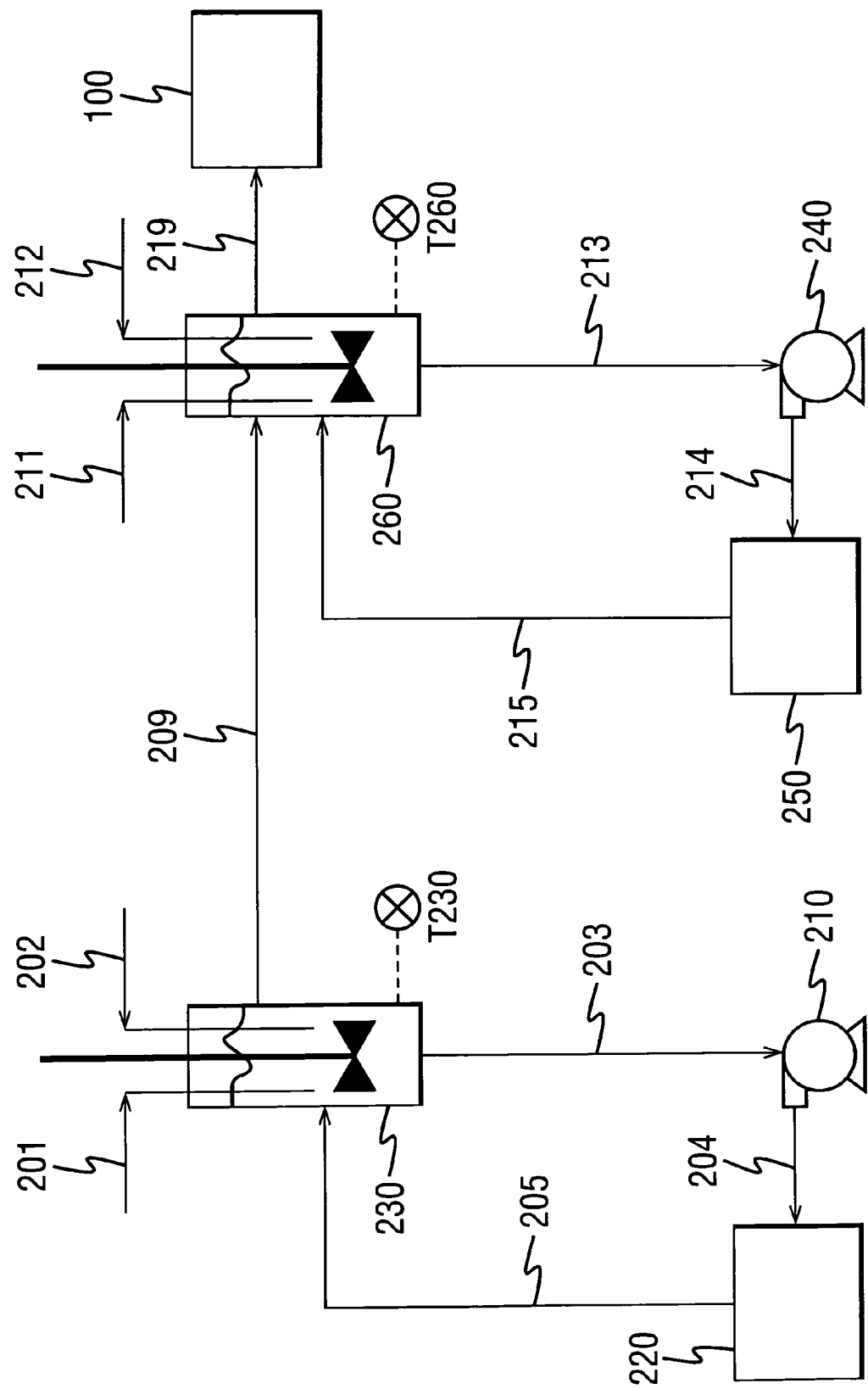

Additional features and advantages will become apparent from the following detailed description of various embodiments of the present invention, considered in conjunction with the accompanying drawings, in which like reference numbers indicate like features, and wherein:

FIG. 1 is a schematic representation of an embodiment of the present invention wherein the reaction process is a hydrolysis reaction of acetone cyanohydrin with acid; and FIG. 2 is a schematic representation of a known prior art process for hydrolysis of acetone cyanohydrin with acid, provided for comparison.

As discussed hereinabove, cyanohydrins are subject to decomposition when in the presence of strong acids at elevated temperatures, for example at temperatures greater than about 70° C., thereby resulting in reduced process yields. Furthermore, in the context of a hydrolysis reaction of acetone cyanohydrin ("ACH") with sulfuric acid, the decomposition of acetone cyanohydrin to acetone and hydrogen cyanide not only results in reducing the yield of hydrolysis products and, in turn, of the downstream MAA and MAA ester products, but it can also lead to additional complications in the hydrolysis system.

For example, the hydrogen cyanide formed by decomposition of acetone cyanohydrin is rapidly hydrolyzed and converted to formamide in the hydrolysis reaction. Subsequently and at a slower rate, the formamide thermally cracks to form carbon monoxide (CO) gas and ammonium sulfate salt. Unless the product mixture is adequately degassed, the presence of CO may manifest itself as pump cavitation and may contribute to overall process and unit inoperability. Increases in the overall temperature of the process can aid in the degassing process, however, increased hydrolysis reaction temperature leads to increased the levels of decomposition of acetone cyanohydrin.

Additionally, under the typical operating conditions described in Kirk-Othmer, Encyclopedia of Chemical Technology, acetone is sulfonated by sulfuric acid to a mixture of mono- and di-sulfonic acids. In the hydrolysis section, acetone monosulfonic acid ("AMSA") predominates and as the reaction progresses further, acetone disulfonic acid ("ADSA") increases and becomes predominant. This series of reactions is important because each sulfonation of acetone reaction is accompanied by the stoichiometric generation of water. As is well-known in the art and pointed out in US '093, where water is present in the hydrolysis reaction mixture it will react to convert SIBAM to HIBAM, which is more difficult and requires higher temperatures to convert to MAM in the subsequent cracking reaction.

In a general embodiment, the method of the present invention for minimizing decomposition of cyanohydrins in an exothermic reaction process involving cyanohydrins, comprises the steps of providing a reaction medium to a tubular reactor and providing one or more reactants to the tubular reactor. The tubular reactor contains at least one reaction zone therein and has internal mixing means positioned in the at least one reaction zone. The method of the present invention further comprises mixing the reaction medium with the one or more reactants in the at least one reaction zone. This mixing forms a bulk reaction mixture having a substantially homogenous composition and a substantially homogenous reaction temperature. The method also comprises removing a quantity of heat from the exothermic reaction process, where the quantity of heat removed is equivalent to the quantity of heat produced by the exothermic reaction process. The quantities of heat removed and produced are equivalent, for purposes of the present invention, where the quantities are about equal to one another, within + or −10%, or even for example, 1%. Lastly, the method of the present invention comprises the step of reacting the one or more reactants in the at least one reaction zone to produce a mixed product having a bulk temperature. The bulk temperature of the mixed product is optimally measured after the reaction has ceased (such as, for example, when substantially all of at least one of the one or more reactants has been reacted) and the mixed product has exited the tubular reactor.

By an exothermic reaction process "involving cyanohydrins" it is meant that one or more of the reactants and products of the reaction processes comprise one or more cyanohydrins. Moreover, as will be recognized by persons of ordinary skill, an exothermic reaction is a reaction which produces a quantity of heat, where the quantity depends upon a number of factors, including but not limited to, the types and amounts of reactants and the temperature and duration of the reaction.

The term "cyanohydrins" as used herein means compounds having the general formula:

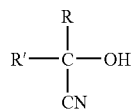

wherein R and R' may be the same or different and are selected from the group consisting of hydrogen and hydrocarbons. The structure of the hydrocarbons is not particularly limited and may comprise straight chains, branched chains, aromatic rings, etc. and the hydrocarbons may be saturated, substituted, or unsaturated. In addition, R and R' together may form part of an alicyclic or heterocyclic moiety.

With respect to the tubular reactor, the method of the present invention includes embodiments wherein there is more than one tubular reactor, or even a plurality of tubular reactors (such as, for example, in a shell-and-tube type of reactor apparatus), used to perform the exothermic reaction process involving cyanohydrins. Where more than one tubular reactor is employed, at least one, and preferably all of the tubular reactors contain at least one reaction zone therein and have internal mixing means positioned in the at least one reaction zone.

Moreover, the internal mixing means of the tubular reactor is at least one device selected from the group consisting of: static mixers comprising static mixing elements, orifice plates, venturis, jet mixers, eductors, perforated plates, spargers, agitators, rotary mixers, high-velocity circulation loops, and spray nozzles. The static mixing elements may be one or more elements selected from the group consisting of blades, pins, baffles, tabular inserts, and other shear-inducing devices. Such devices and static mixing elements are well known and commercially available from companies such as Koch-Glitsch, Inc. of Wichita, Kans., Chemineer, Inc. of Dayton, Ohio, and Sulzer Chemtech Ltd. of Tulsa, Okla.

As will be recognized by persons of ordinary skill in the art, where the reaction process involves the use of corrosive substances (such as for example, sulfuric acid or caustic), the tubular reactor and its internal mixing means should be constructed of corrosion resistant materials, including but not limited to stainless steel (e.g., 300 series, 904L, 6-moly), tantalum, zirconium, and HASTELLOY® (e.g., B, B-2, B-3, C-22, and C-276).

The reaction medium may be any material suitable for mixing with, containing, and transporting the reactants of the desired chemical reaction, without being consumed by the reaction, and will depend upon the nature of the desired chemical reaction and the required reactants. For example, without limitation, a suitable reaction medium may comprise the same types of compounds as are expected to be produced by the reaction process involving cyanohydrins. In fact, the reaction medium may be suitably comprised of captured and recycled products of the reaction process. Thus, in the case of a hydrolysis reaction of acetone cyanohydrin and sulfuric acid which is expected to produce SIBAM, HIBAM and MAM, the reaction medium could suitably comprise one or more of SIBAM, HIBAM and MAM. In some embodiments, the reaction medium may further comprise diluent materials, such as for example, hexane, sulfur dioxide, or straight-chain hydrocarbons.

It is understood that one or more of the reactants (such as, for example, the acid in a hydrolysis reaction) may be provided indirectly to the tubular reactor by first adding one or more of the reactants to the reaction medium prior to providing the reaction medium to the tubular reactor.

The one or more reactants used for the reaction process will depend upon the desired reaction and reaction products and it is well within the ability of persons of ordinary skill to select suitable reactants. For example, where it is desired to make SIBAM, HIBAM and MAM for further conversion to MAA and esters thereof, suitable reactants may be acetone cyanohydrin and an acid selected from the group consisting of sulfuric acid, oleum and mixtures thereof (as disclosed in US '093 discussed earlier hereinabove). Where acetone cyanohydrin is itself the desired product, the reactants may be acetone and hydrogen cyanide (as described in Kirk-Othmer, Encyclopedia of Chemical Technology), and a strong base, such as sodium hydroxide, may be present. In this reaction, water may also be present as a diluent, and the reaction may be typically performed between 0° C. and 20° C., with elevated temperatures (greater than about 20° C.) promoting cyanohydrin decomposition in this reaction system. Where it is desired to produce a particular cyanohydrin known as methyl ethyl ketone cyanohydrin, the reactants may be hydrocyanic acid and methyl ethyl ketone (as disclosed in U.S. Pat. No. 6,743,938), and the reaction may be performed in the presence of a strong base, such as diethylamine. Thus, the cyanohydrin may be the reactant or the product in the reaction process and the method of the present invention may be advantageously applied to any such exothermic reaction process involving cyanohydrins.

The step of mixing the reaction medium with the one or more reactants to form a bulk reaction mixture having a substantially homogenous composition and a substantially homogenous reaction temperature is accomplished, at least in part, in accordance with the present invention, by the use of the tubular reactor having internal mixing means described hereinabove.

Another way to rapidly and thoroughly mix the reaction medium and one or more reactants to form a homogenous bulk reaction mixture, in accordance with the present invention, would be to provide at least one of the reactants to the tubular reactor at a plurality of points of addition, using a plurality of injector devices, such as without limitation, injector nozzles, that are positioned about the tubular reactor apparatus. The injector devices may be positioned about the tubular reactor circumferentially, longitudinally, or both. Moreover, all of the injector devices need not be used at any given time, but rather, at least one, and preferably more than one injector device should be in use to provide at least one of the reactants to the tubular reactor at various different points of addition. This arrangement serves to distribute the reactant more evenly into the reaction medium. In a particular embodiment of the present invention, the injection velocity of the reactant or reactants being provided through the injector devices may be the same at each injector device being used. Additionally, the injection velocity of the reactant(s) may be maintained, for example, without limitation, between 10 ft/sec and 80 ft/sec (3 m/sec and 24 m/sec), or between 20 ft/sec and 65 ft/sec (6 m/sec and 20 m/sec), or even between 28 ft/sec and 42 ft/sec (8.5 m/sec and 13 m/sec), to achieve efficient mixing.

It is also possible, in accordance with the present invention, to maintain optimal mixing efficiency using the injector devices by operating fewer injectors at lower overall production rates and, similarly, by operating more of the injector devices at higher production rates, rather than using the same number of injector devices at all times and adjusting the flow rate through each nozzle. The former procedure is believed to be better than the latter procedure because the latter procedure would result in variable injection velocities and, therefore, variable mixing efficiencies, at different locations within the reaction zones. For example, operating 10 injector devices at different injection velocities to achieve an overall reactant feed rate of 100 pounds per hour would create variable mixing conditions in the tubular reactor and a non-homogenous bulk reaction mixture. Operating 10 injector devices each at 10 pounds per hour would achieve more uniform mixing and a more homogenous bulk reaction mixture. If a decision is made to decrease the production rate such that only a feed rate of 50 pounds per hour of reactant is required, then only 5 of the injector devices could be operated, each at the same 10 pounds per hour, while the other 5 injector devices are disabled or turned off, thus maintaining uniformity of mixing within the tubular reactor. It is believed that further optimization of the foregoing procedures, as well as the calculations and conversions required to determine the optimal injector operation procedure, are well within the ability of persons of ordinary skill in the art.

In a particular embodiment of the present invention, which is a hydrolysis reaction of acetone cyanohydrin with sulfuric acid, the addition rate of a reactant, such as acetone cyanohydrin, is controlled such that the temperature at the point of addition is never greater than the bulk temperature of the mixed product which leaves the tubular reactor. This serves to minimize, or even eliminate, the hot spots which may otherwise develop at the point of addition of the reactants through the injector devices.

As with most exothermic reactions, the heat produced by the exothermic reaction process involving cyanohydrins must be removed in order to sustain the reaction process over time in a continuous steady state. The heat may be removed by cooling the tubular reactor, which will of course also cool the reaction zones and the bulk reaction mixture therein, using any conventional cooling means such as for example, any one or more of the following devices: shell-and-tube heat exchangers, spiral coolers, plate-and-frame exchangers, jacketed piping sections, and vessels with internal coiling coils or jacketing. It is possible to use turbulators in the tubes of shell-and-tube heat exchangers to improve cooling efficiency and/or resist fouling.

In accordance with the present invention, heat may also be removed from the exothermic reaction process by cooling the reaction medium to a temperature between 1° C. and 10° C. less than the bulk temperature of the mixed product prior to providing the reaction medium to the tubular reactor. This aspect of the present invention results in the formation of a cooled bulk reaction mixture upon mixing the reactants with the reaction medium in the at least one reaction zone of the tubular reactor, which provides a cooler environment for the cyanohydrin, regardless of whether the cyanohydrin is a reactant that is added, or a product that is formed, in the reaction zone.

Additionally, it is advantageous to remove heat from the cyanohydrins while they are in the at least one reaction zone with the reaction medium to minimize their decomposition. In accordance with the method of the present invention, this can be accomplished, at least in part, by providing an excess of reaction medium to the at least one reaction zone in comparison to the amount of reactants provided, whereupon the reaction medium becomes a heat sink and absorbs some of the heat from the cyanohydrins. For example, the reaction medium and the one or more reactants may be provided at a ratio of reaction medium:reactants of between 2:1 and 200:1, or between 3:1 and 100:1, or even between 4:1 to 40:1. It is noted that higher reaction medium:reactants ratios are better because they are believed to provide a larger heat sink capable of absorbing greater quantities of heat.

In another embodiment of the present invention, one or more of the reactants may be cooled prior to being provided to the tubular reactor, for example, using separate heat exchangers (not shown).

Where the exothermic reaction process involving cyanohydrins is a hydrolysis reaction of acetone cyanohydrin and sulfuric acid which produces a mixed product comprising SIBAM, HIBAM, and MAM, as previously discussed, for further reaction to produce MAA and esters thereof, the method may further comprise thermally converting the mixed product from the hydrolysis reaction in a cracker reactor to produce a cracker reactor mixture comprising methacrylamide and methacrylic acid. The cracker reactor mixture may then be reacted in at least one reactor with a material selected from alkanols and water to produce a monomer selected from methacrylic acid and esters thereof. Examples of suitable alkanols include but are not limited to methanol, ethanol, and butanol.

In addition, to the foregoing features, it is possible for persons of ordinary skill in the art to recognize and develop many additions and modifications to the method of the present invention, all of which are intended to be within the scope of the invention. For example, where the exothermic reaction process is a hydrolysis reaction of acetone cyanohydrin with sulfuric acid, the reaction process may be a two stage system, i.e., having two tubular reactors and where the acetone cyanohydrin reactant feed is split between the two reactors, with between 50% and 95% of the acetone cyanohydrin reaction being provided to the first reactor, and the remainder to the second reactor.

As might be recognized by persons of ordinary skill, the reaction processes involving cyanohydrins may also involve the need to transport and pump process streams which are highly viscous. One or more of the reaction medium and the mixed product may be transported and circulated through and between the process apparatus using high-viscosity service pumps, such as, but not limited to, Disc pumps (commercially available from Discflo Corporation of Santee, Calif.), positive displacement pumps, or gear pumps. One or more of the reactants, such as the acid in a hydrolysis reaction, may be injected into the reaction medium prior to providing the reaction medium to the tubular reactor to provide higher localized mole ratios and to reduce the viscosity effects.

Conditions in the reaction process, such as where the reaction process is a hydrolysis reaction of acetone cyanohydrin with sulfuric acid, may make degassing of the mixed product advantageous. In such circumstances, any conventional degassing means is suitable, including but not limited to, one or more devices selected from the group consisting of: impingement plates, coalescers, baffles, centrifugal separators (such as "Porta-Test Revolution" degassers, from NATCO Group, Inc. of Houston, Tex.), vacuum chambers, distributors, nozzles, throttling valves, flash tanks, settling chambers, ASP-type Degassing Pumps (commercially available from Yokota Manufacturing Co., Ltd. of Hiroshima, Japan), and the Kurabo In-line Degassing Device (available from Kurabo Industries Ltd. of Osaka, Japan).

As would be easily determinable by persons of ordinary skill in the art, it may also be advantageous to add one or more polymerization inhibitors to the reaction process, such as, for example, to one or more of the reactants prior to providing them to the tubular reactor. Suitable polymerization inhibitors will depend, at least in part, upon the types of reactants and products involved in the reaction process. For example, where the exothermic reaction process is a hydrolysis reaction of acetone cyanohydrin with sulfuric acid, a suitable inhibitor would include, but not be limited to, phenothiazine.

Furthermore, where the exothermic reaction process is a hydrolysis reaction of acetone cyanohydrin with sulfuric acid, the molar ratio of acid:acetone cyanohydrin present in the bulk reaction mixture is in the range of from 1.3:1 to 1.9:1

These and other similar modifications will readily suggest themselves to those skilled in the art, and are intended to be encompassed within the spirit of the present invention disclosed herein and the scope of the appended claims.

EXAMPLES

The following Examples provide comparative yields for two commercial-scale hydrolysis reaction processes operating at identical conditions. The results of these Examples demonstrate the yield advantage afforded by the method of the present invention over the prior art CSTR-based reaction processes involving cyanohydrins, particularly when applied to a hydrolysis reaction of acetone cyanohydrin with sulfuric acid. The compositions of the acetone cyanohydrin reactant and sulfuric acid reactant were the same for both Example 1 and Example 2.

Example 1

Comparative—Prior Art Process

A first hydrolysis process ("Prior Art") of the type disclosed in Kirk-Othmer and US '093 is illustrated by FIG. 2, and comprised two CSTR reactors in series. This system was operated at an H2SO4:ACH molar ratio of 1.48, and at a 2.3:1 ACH addition split, wherein 70% by weight of the total ACH feed was added to the first reaction stage, and 30% by weight of the total ACH feed was added to the second reaction stage. Sulfuric acid at a concentration of 99.5% and ACH at a concentration of 98.5% were utilized as reactants in this system.

Specifically, the $1^{st}$ reaction stage of the hydrolysis system employed in this example comprised a $1^{st}$ stage CSTR 230, a centrifugal pump 210, a heat exchanger 220, and associated $1^{st}$ stage circulation piping (203,204,205). CSTR 230 comprised a 5000 gal (19 cubic meters) vessel and a dual-impeller, pitched-blade agitator for high-efficiency mixing of the reactor contents. Sub-surface ACH addition to the $1^{st}$ stage CSTR 230 was provided via 201 using a first dip-pipe. Similarly, Sub-surface Sulfuric Acid addition to the $1^{st}$ stage CSTR 230 was provided via 202 using a second dip-pipe. These dip-pipes served to direct the flow of reactants into the turbulent zone near the tip of the agitator blades in order to maximize efficiency of the mixing. PTZ inhibitor in acetone solution (not shown) was also added into CSTR 230 to retard polymer formation. The temperature of the bulk liquid in the bottom of CSTR 230 could be monitored using thermocouple T230.

Stream 203 provides hydrolysis mix to Pump 210, which then circulated hydrolysis mix through the $1^{st}$ stage circulation piping at a continuous rate of about 2.8 million lbs/hr (i.e., 4000 gpm, 15,140 liters/min). Stream 204 conveyed the hydrolysis mix from the discharge of pump 210 to heat exchanger 220, where it was cooled. Heat exchanger 220 was a shell-and-tube type exchanger, with the process flow (hydrolysis mix) passing through the shell side and a nominal 60° C. tempered water flow passing through the tube side. Cooled hydrolysis mix exited the heat exchanger via stream 205 and was returned to CSTR 230. Gases removed from the hydrolysis mix were vented to a process flare header (not shown) for disposal. Degassed hydrolysis mix overflowed from the side of CSTR 230 and was conveyed forward to the $2^{nd}$ reaction stage via stream 209.

The $2^{nd}$ reaction stage of the hydrolysis system employed in this example comprised a $2^{nd}$ stage CSTR 260, a centrifugal pump 240, a heat exchanger 250, and associated 2 stage circulation piping (213,214,215). CSTR 260 comprised a 5000 gal (19 cubic meters) vessel and a dual-impeller, pitched-blade agitator for high-efficiency mixing of the reactor contents. Sub-surface ACH addition to the $2^{nd}$ stage CSTR 230 was provided via 211 using a first dip-pipe. Optional Sub-surface Sulfuric Acid (212) addition to the $2^{nd}$ stage CSTR 230 was not used in this example. As with the $1^{st}$ stage CSTR dip-pipes, these $2^{nd}$ stage dip-pipes served to direct the flow of reactants into the turbulent zone near the tip of the agitator blades in order to maximize efficiency of the mixing. The temperature of the bulk liquid in the bottom of CSTR 260 could be monitored using thermocouple T260.

Stream 213 provided hydrolysis mix to Pump 240, which then circulated hydrolysis mix through the $2^{nd}$ stage circulation piping at a continuous rate of about 4.2 million lbs/hr (i.e., 6000 gpm, 22,700 liters/min). Stream 214 conveyed the hydrolysis mix from the discharge of pump 240 to heat exchanger 250, where it was cooled. Heat exchanger 250 was a shell-and-tube type exchanger, with the process flow (hydrolysis mix) passing through the shell side and a nominal 65° C. tempered water flow passing through the tube side. Cooled hydrolysis mix exited the heat exchanger via stream 215 and was returned to CSTR 260. Gases removed from the hydrolysis mix were vented to a process flare header (not shown) for disposal. Degassed hydrolysis mix overflowed from the side of CSTR 260 and was conveyed forward to the cracker reactor (100) via Stream 219.

In this example, the bulk temperature of the reaction mixture exiting the $1^{st}$ reaction stage CSTR (230), as measured by thermocouple T230, was held constant at 85° C.; the bulk temperature of the reaction mixture exiting the $2^{nd}$ reaction stage CSTR (260), as measured by thermocouple T260, was held constant at 101° C.

Under steady state conditions, samples of the final hydrolysis mix were collected from stream 219 using well-insulated sample containers (Thermos™ brand vacuum bottles).

An aliquot (~10 g) of the representative Hydrolysis mix was removed and placed in a tared jar containing a stir bar and its weight was recorded. Methanesulfonic acid (99.5% purity, ~3 g, from Aldrich Chemical Company) was added as an internal standard via a syringe and the weights were all recorded. The mixture was stirred in a constant temperature water bath at 60° C. for 40 min. An aliquot (~0.2 g) of the resulting mixture was removed and placed in an NMR tube and diluted with deuterated nitromethane ($CD_3NO_2$, from Aldrich Chemical Company). The clear and homogeneous mixture was analyzed by NMR on a Varian Inova 500 Instrument.

The total molar yield of SIBAM, HIBAM and MAM produced by the foregoing process is reported in Table 1.

Example 2

An improved hydrolysis system ("Inventive"), in accordance with the method of the present invention, is illustrated in FIG. 1 and comprised two continuous flow reaction stages. This system was operated under the same conditions used for the CSTR-based hydrolysis system of the preceding Example 1.

Specifically, this improved hydrolysis system was operated at an H2SO4:ACH molar ratio of 1.48, and at a 2.3:1 ACH addition split, wherein 70% by weight of the total ACH feed was added to the first reaction stage and 30% by weight of the total ACH feed was added to the second reaction stage. As in the previous example, Sulfuric acid at a concentration of 99.5% and ACH at a concentration of 98.5% were utilized as reactants.

The $1^{st}$ reaction stage of the hydrolysis system employed in this example comprised an ACH mixing apparatus 10, a degassing apparatus 20, a centrifugal pump 30, a heat exchanger 40, and associated $1^{st}$ stage circulation piping (3,4, 5,7,8). Sulfuric Acid (6) was added into the hydrolysis mix in stream 5 through a mixing tee. Stream 5 provided hydrolysis mix to Pump 30, which then circulated hydrolysis mix through the $1^{st}$ stage circulation piping at a continuous rate of about 2.5 million lbs/hr (i.e., 3500 gpm, 13,250 liters/min). Stream 7 conveyed the hydrolysis mix from the discharge of pump 30 to heat exchanger 40, where it was cooled. Heat exchanger 40 was a shell-and-tube type exchanger, with the process flow (hydrolysis mix) passing through the shell side and a nominal 60° C. tempered water flow passing through the tube side. Cooled hydrolysis mix exited the heat exchanger via stream 8. The temperature of the cooled hydrolysis mix could be monitored using thermocouple T8. The hydrolysis mix then entered the ACH mixing apparatus 10, wherein ACH was added into the hydrolysis mix stream. The ACH mixing apparatus 10 comprised a single static mixing unit consisting of four Koch SMXL mixing elements (available from Koch-Glitsch, Inc. of Wichita, Kans.) installed in series within a 12" diameter piping section. The static mixing unit was approximately 190 inches in length. The ACH mixing apparatus 10 further comprised two sets of ACH injectors: a first set of four injectors 11 located at a distance of about 30" from the inlet end of the mixing apparatus and a second set of four injectors 12 located at a distance of about 45" from the inlet end of the mixing element. Each of the four injectors in a set were evenly-spaced along the circumference of the pipe section— e.g., one injector each positioned at 0°, 90°, 180°, and 270° relative to the pipe section centerline. Each injector comprised a 0.290" internal diameter orifice, flush-mounted to the piping section wall, through which liquid ACH flowed at a velocity of about 36 feet per second (11 meters per second) into the static mixing unit. At this velocity, a jet of ACH was produced having sufficient kinetic energy to traverse from the pipe section wall toward the centerline of the static mixing unit, thereby ensuring rapid and efficient mixing. For the operating rate of this specific example, six of the eight injectors were utilized: all four of the first set of injectors and two of the second set of injectors. Of the injectors in operation, all were operated at the same ACH flow rate. As a result of the exothermic ACH hydrolysis reaction, the hydrolysis mix warmed within the ACH mixing apparatus. The warm hydrolysis mix exited the ACH mixing apparatus via stream 3 and entered the degassing apparatus 20. PTZ inhibitor in acetone solution (9) was added into the hydrolysis mix stream 3 to retard polymer formation.

Degassing apparatus 20 comprised an unagitated 5,600 gallon (21 cubic meters) degassing vessel in which was installed a "Porta-Test Revolution" model centrifugal gas/liquid separator (designed and manufactured by NATCO Group, Inc. of Houston, Tex.). Gases removed from the hydrolysis mix were vented to a process flare header (not shown) for disposal; the degassed hydrolysis mix collected as a bulk liquid in the bottom of the degassing vessel. The temperature of the bulk liquid in the bottom of the degassing vessel could be monitored using thermocouple T20. Degassed hydrolysis mix was withdrawn from the bottom of the degassing vessel and was divided into two streams: stream 49 conveyed a first portion of the hydrolysis mix forward to the $2^{nd}$ reaction stage, while stream 5 returned a second portion of the hydrolysis mix to centrifugal pump 30 to maintain the $1^{st}$ stage circulation.

The $2^{nd}$ reaction stage of the inventive hydrolysis system employed in this example comprised an ACH mixing apparatus 50, a degassing apparatus 60, a centrifugal pump 70, a heat exchanger 80, and associated $2^{nd}$ stage circulation piping (13,14,15,17,18). Hydrolysis mix from stream 49 entered the $2^{nd}$ stage and was combined with the hydrolysis mix in stream 15. In this specific example, optional sulfuric acid (16) was not added. Stream 15 provided hydrolysis mix to Pump 70, which then circulated hydrolysis mix through the $2^{nd}$ stage circulation piping at a continuous rate of about 2.2 million lbs/hr (i.e., 3000 gpm, 11,360 liters/min). Stream 17 conveyed the hydrolysis mix from the discharge of pump 70 to heat exchanger 80, where it was cooled. Heat exchanger 80 was a shell-and-tube type exchanger, with the process flow (hydrolysis mix) passing through the tube side and a nominal 70° C. tempered water flow passing through the shell side. Cooled hydrolysis mix exited the heat exchanger via stream 18. The temperature of the cooled hydrolysis mix could be monitored using thermocouple T18. The hydrolysis mix then entered the ACH mixing apparatus 50, wherein ACH was added into the hydrolysis mix stream. The ACH mixing apparatus 50 comprised a single static mixing unit consisting of four Koch SMXL mixing elements installed in series within a 12" diameter piping section. The static mixing unit was approximately 210 inches in length. The ACH mixing apparatus 50 further comprised two sets of ACH injectors: a first set of four injectors 11 located at a distance of about 30" from the inlet end of the mixing apparatus and a second set of four injectors 12 located at a distance of about 45" from the inlet end of the mixing element. Each of the four injectors in a set were evenly-spaced along the circumference of the pipe section—e.g., one injector each positioned at 0°, 90°, 180°, and 270° relative to the pipe section centerline. Each injector comprised a 0.175" internal diameter orifice, flush-mounted to the piping section wall, through which liquid ACH flowed at a velocity of about 62 feet per second (19 meters per second) into the static mixing unit. At this velocity, a jet of ACH was produced having sufficient kinetic energy to traverse from the pipe section wall toward the centerline of the static mixing unit, thereby ensuring rapid and efficient mixing. For the operating rate of this specific example, only the first set of four injectors were utilized; of the injectors in operation, all were operated at the same ACH flow rate. As a result of the exothermic ACH hydrolysis reaction, the hydrolysis mix warmed within the ACH mixing apparatus. The warm hydrolysis mix exited the ACH mixing apparatus via stream 13 and entered the degassing apparatus 60. In this specific example, optional PTZ inhibitor in acetone solution (19) was not added.

Degassing apparatus 60 comprised an unagitated 10,900 gallon (41 cubic meters) degassing vessel in which was installed a "Porta-Test Revolution" model centrifugal gas/liquid separator (designed and manufactured by NATCO Group, Inc. of Houston, Tex.). Gases removed from the hydrolysis mix were vented to a process flare header (not shown) for disposal; the degassed hydrolysis mix collected as a bulk liquid in the bottom of the degassing vessel. The temperature of the bulk liquid in the bottom of the degassing vessel could be monitored using thermocouple T60. Degassed hydrolysis mix was withdrawn from the bottom of the degassing vessel (14) and was divided into two streams: stream 99 conveyed a first portion of the hydrolysis mix forward to the cracker reactor (100), while stream 15 returned a second portion of the hydrolysis mix to centrifugal pump 70 to maintain the $2^{nd}$ stage circulation.

In this example, the bulk temperature of the reaction mixture exiting the $1^{st}$ stage degassing apparatus (20), as measured by thermocouple T20, was held constant at 85° C.; the bulk temperature of the reaction mixture exiting the $2^{nd}$ stage degassing apparatus (60), as measured by thermocouple T60, was held constant at 101° C.

Under steady state conditions, samples of the final hydrolysis mix were collected from stream 99 using well-insulated sample containers (Thermos™ brand vacuum bottles).

As in the previous example, the hydrolysis mix sample was acidified, diluted, and analyzed by NMR. The total molar yield of SIBAM, HIBAM and MAM produced by the foregoing inventive method is reported in Table 1.

TABLE 1

| Hydrolysis System | Stream Temperature at ACH Feed point | | Residence Time | ACH Molar Yield (%) |
|---|---|---|---|---|
| | $1^{st}$ stage | $2^{nd}$ stage | | |
| Example 1 (Prior Art CSTR) (FIG. 2) | 85° C. (T230) | 101° C. (T260) | 40 minutes | 95.23 ± 0.60 |
| Example 2 (Inventive Method) (FIG. 1) | 79° C. (T8) | 100° C. (T18) | 110 minutes | 96.01 ± 0.22 |

This comparative example illustrates that the inventive continuous flow reaction system provides a higher ACH yield than the prior-art CSTR-based system when used to perform ACH Hydrolysis reactions.

We claim:

1. A method for minimizing decomposition of cyanohydrins in an exothermic reaction process which produces cyanohydrins and a quantity of heat, said cyanohydrins being selected from the group consisting of acetone cyanohydrin and methyl ethyl ketone cyanohydrin, said method comprising the steps of:
    (a) providing a reaction medium to a tubular reactor containing at least one reaction zone therein and having internal mixing means positioned in said at least one reaction zone;
    (b) providing one or more reactants to said tubular reactor;
    (c) mixing said reaction medium with said one or more reactants in said at least one reaction zone, thereby forming a bulk reaction mixture having a substantially homogenous composition and a substantially homogenous reaction temperature;
    (d) removing a quantity of heat from the exothermic reaction process, said quantity of heat being equivalent to said quantity of heat produced by the exothermic reaction process; and
    (e) reacting said one or more reactants in said at least one reaction zone to produce a mixed product having a bulk temperature.

2. The method of claim 1, wherein the step of removing a quantity of heat is performed by cooling said reaction medium to a temperature between 1° C. and 10° C. less than said bulk temperature prior to providing said reaction medium to said tubular reactor.

3. The method of claim 1, wherein said internal mixing means is at least one device selected from the group consisting of: static mixers, orifice plates, venturis, jet mixers, eductors, perforated plates, spargers, agitators, rotary mixers, high-velocity circulation loops, and spray nozzles.

4. The method of claim 1, wherein said tubular reactor comprises at least two tubular reactors.

5. The method of claim 3, wherein the static mixer comprises one or more mixing element selected from the group consisting of: blades, pins, baffles, tabular inserts, and other shear-inducing devices.

6. The method of claim 1, wherein the cyanohydrins produced comprise acetone cyanohydrin, and wherein said one or more reactants comprise a first reactant comprising acetone and a second reactant comprising hydrogen cyanide.

7. The method of claim 1, wherein the cyanohydrins produced comprise methyl ethyl keton cyanohydrin, and wherein said one or more reactants comprises a first reactant comprising methyl ethyl ketone and a second reactant comprising hydrogen cyanide.

8. The method of claim 1, wherein a strong base is present.

9. The method of claim 8, wherein said strong base is selected from the group consisting of sodium hydroxide and diethylamine.

10. The method of claim 1, wherein said exothermic reaction is performed between 0° C. and 20° C.

11. The method of claim 1, wherein said step of removing a quantity of heat from the exothermic reaction process is accomplished using one or more devices selected from the group consisting of: a shell-and-tube heat exchanger, a spiral cooler, a plate-and-frame heat exchanger, a jacketed piping section, a vessel with internal cooling coils and a vessel with external jacketing.

12. The method of claim 11, wherein a shell-and-tube heat exchanger includes the tubular reactor and the device for removing a quantity of heat.

* * * * *